US010725006B2

(12) United States Patent
Huber et al.

(10) Patent No.: US 10,725,006 B2
(45) Date of Patent: Jul. 28, 2020

(54) MASS SPECTROMETER METHOD AND APPARATUS FOR MONITORING FOR TATP (71) Applicant: RJ LEE GROUP, INC., Monroeville, PA (US)

(72) Inventors: Heinz J. Huber, Novelty, OH (US); Richard J. Lee, Murrysville, PA (US)

(73) Assignee: RJ LEE GROUP, INC., Monroeville, PA (US)

( * ) Notice: Subject to any disclaimer, the term of this patent is extended or adjusted under 35 U.S.C. 154(b) by 22 days.

(21) Appl. No.: 15/904,471

(22) Filed: Feb. 26, 2018

(65) Prior Publication Data
US 2019/0265216 A1    Aug. 29, 2019

(51) Int. Cl.
| H01J 49/26 | (2006.01) |
| H01J 49/14 | (2006.01) |
| G01N 33/00 | (2006.01) |
| H01J 49/00 | (2006.01) |
| G01N 27/62 | (2006.01) |
| H01J 49/04 | (2006.01) |
| H01J 49/24 | (2006.01) |

(52) U.S. Cl.
CPC ......... G01N 33/0057 (2013.01); G01N 27/62 (2013.01); H01J 49/0031 (2013.01); H01J 49/0422 (2013.01); H01J 49/145 (2013.01); H01J 49/24 (2013.01)

(58) Field of Classification Search
CPC ...... G01N 33/0057; G01N 27/62; H01J 49/00
See application file for complete search history.

(56) References Cited

U.S. PATENT DOCUMENTS

| 5,838,003 A | 11/1998 | Bertsch et al. |
| 6,979,816 B2 | 12/2005 | Tang et al. |
| 7,829,345 B1 | 11/2010 | MacDonald |
| (Continued) | | |

FOREIGN PATENT DOCUMENTS

| WO | WO2014053540 A1 | 10/2014 |
| WO | WO2016141403 A1 | 9/2016 |

OTHER PUBLICATIONS

Shen et al., 'Triacetone triperoxide detection using low reduced-field proton transfer reaction mass spectrometer', May 3, 2009, Intl. Journal of Mass Spec., 285 (100-103).*

(Continued)

Primary Examiner — Eliza W Osenbaugh-Stewart
(74) Attorney, Agent, or Firm — Eckert Seamans Cherin & Mellott, LLC; Arnold B. Silverman (57) ABSTRACT

Methods and apparatus for monitoring air samples for the presence of the explosive TATP are disclosed. A preferred approach employs proton transfer reaction mass spectrometry PTR-MS). The system may be operated continuously on a real time or near real time basis. A delivery tube of specific dimensions and materials is employed to introduce the sample into the ionization chamber which in turn generates the ions which are delivered to the mass spectrometer for determining the m/z values. The system may employ a plurality of ionization chambers to reduce the amount of false negative identifiers. A multiple inlet ion funnel may be employed to combine the ions from each of the ionization chambers. Chemical ionization may be employed. A validation module may be employed to reduce the amount of false positive identifiers.

60 Claims, 8 Drawing Sheets

(56) References Cited

U.S. PATENT DOCUMENTS

| | | | |
|---|---|---|---|
| 2009/0095901 A1 | 4/2009 | Robinson et al. | |
| 2012/0091335 A1* | 4/2012 | Thompson | G01N 1/02 250/288 |
| 2013/0260478 A1 | 10/2013 | Ewing et al. | |
| 2015/0177214 A1 | 6/2015 | Vilkov et al. | |
| 2015/0249000 A1* | 9/2015 | Sulzer | H01J 49/0031 250/282 |
| 2015/0318161 A1 | 11/2015 | Brown et al. | |
| 2018/0329108 A1* | 11/2018 | Gonsky, Jr. | G01V 5/0075 |

OTHER PUBLICATIONS

Jordan et al., 'A high resolution and high sensitivity proton-transfer-reaction time-of-flight mass spectrometer (PTR-TOF-MS)', Jul. 24, 2009, Intl. Journal of Mass Spec., 286 (122-128).*

Ennis et al. 'A hollow cathod proton transfer reaction time of flight mass spectrometer', Nov. 2, 2005, Int. Journal of Mass Spec., 247 (72-80).*

Mäkinen M., et al. Ion Spectrometric detection technologies for ultra-traces of explosives: a review. (2011) Mass Spectrom. Rev. 30, 940-973; Wiley Periodicals, Inc.; Mikkeli, Finland.

Triacetone Triperoxide (TATP)—GlobalSecurity.org www.globalsecurity.org . Military Systems > Munitions > Introduction > Explosives Jul. 7, 2011 (assessed Dec. 29, 2016).

Giannoukos, et al.; Chemical Sniffing Instrumentation for Security Applications; Chemical Rev. 116; 2016; American Chemical Society; p. 8146-8172.

Mayhew C., et al. Applications of proton transfer reaction time-of-flight mass spectrometry for the sensitive and rapid real-time detection of solid high explosives. (2010); Int. J. Mass Spec. 289, 58-63; Elsevier.

Wolkoff (1995) Volatile Organic Compounds Sources, Measurements, Emissions, and the Impact on Indoor Air Quality. Indoor Air 5, 5-73.

Yinon J. and Zitrin S. (1996) Modern Methods and Applications in Analysis of Explosives. John Wiley & Sons, 316 pp. https://books.google.com/books?isbn=0471965626; (pp. 252-253).

Cotte-Rodriguez, I. and Cooks R.G.; Non-proximate detection of explosives and chemical warfare agent simulants by desorption electrospray ionization mass spectrometry, The Royal Society of Chemistry 2006, Chem. Commun, 20016, 2968-2970, Jun. 2006, Cambridge, UK.

Jürschik S., et al. (2010) Proton transfer reaction mass spectrometry for the sensitive and rapid real-time detection of solid high explosives in air and water. Mass Spectrometry (DGMS 2010); Anal Bioanal Chem. 398, 2813-2828.

Matyas R. and Pachman J. (2016) Primary explosives. Springer, 360 pages.(Chapter 10).

Sulzer P., et al. (2013) Applications of switching reagent ions in proton transfer reaction mass spectrometric instruments for the improved selectivity of explosive compounds. Int. J Mass Spec 354-355, 123-128.

Sulzer P., et al. (2012) Proton Transfer Reaction Mass Spectrometry and the Unambiguous Real-Time Detection of 2,4,6 Trinitrotoluene. Anal. Chem. 84, 4161-4166.

Colizza, K., et al. "Reactions of Organic Peroxides with Alcohols in Atmospheric Pressure Chemical Ionization—the Pitfalls of Quantifying Triacetone Triperoxide (TATP)"; J. Am Soc. Mass Spectrom., vol. 29, p. 393-404. Nov. 7, 2017, entire document.

Shen, C. et al. "Triacetone triperoxide detection using low reduced-field proton transfer reaction mass spectrometer"; International Journal of Mass Spectrometry, vol. 285, p. 100-103 (2009), p. 100, left column, para 1: p. 100, right col, para 2; p. 101, left col, para 2; p. 102, left col, para 2-3; Fig 4b.

* cited by examiner

MASS SPECTROMETER METHOD AND APPARATUS FOR MONITORING FOR TATP

BACKGROUND OF THE INVENTION

1. Field of the Invention

The present invention discloses a method and apparatus for continuous detection of TATP in real-time by pulling ambient air through tubing into analytical standoff instrumentation. The invention is particularly based on the use of specific electronic conditions for a chemical ionization technique in connection with a mass spectrometer

2. Description of the Prior Art

PRIOR ART

Detection of explosives has been a long standing concern of the military and more recently security agencies and has taken on increasing importance with the attacks since September 1. See Mäkinen M., et al. (2011) Ion Spectrometric detection technologies for ultra-traces of explosives: a review. Mass Spectrom. Rev. 30, 940-973.

The non-peaceful use of explosives and their extensive applications in vicious attacks have substantially increased in recent years causing the worldwide threats of terror activity. Information on the synthesis of toxic and explosive materials can nowadays be easily found in the public domain, while raw materials for the synthesis of explosives are commercially available. This results in a growing risk of explosive-based attacks as well as increasing psychological impacts on population. Meanwhile, the research on explosives creates an ever expanding variety of potential materials causing issues for the detection devices. See Triacetone Triperoxide (TATP)—GlobalSecurity.org www.globalsecurity.org> Military>Systems>Munitions>Introduction> Explosives Jul. 7, 2011 (accessed Dec. 29, 2016).

Because of the wide range of energetic materials and the many differences in their physical properties, several detection devices detect only certain types of explosives and fail to detect others. For example, many detection devices readily detect conventional explosives made of organic nitro and nitrate compounds, but fail to detect explosives made of inorganic nitrates or non-nitrogenous compounds. In particular, many nitrogen-based detection devices fail to detect explosives such as ANFO (ammonium nitrate in fuel oil), Black Powder ("gun powder" formed from potassium nitrate, sulfur and charcoal), TATP (triacetone triperoxide) and HMTD (Hexamethylene triperoxide diamine). As a result, such explosives are sometimes referred to as "transparent".

In a 2016 published review article on currently available technologies for explosives detection, the following statement was made. See Giannoukos S., et al. (2016) Chemical Sniffing Instrumentation for Security Applications. Chem. Rev. 116, 8146-8172.

"Demands for real time or near real time accurate chemical analysis increasingly require techniques that operate 'in the field'." Field chemical analysis eliminates sample transportation/storage costs and minimizes sample contamination risks during shipment from a distant site back to the laboratory. In addition to time and cost reduction, field analysis allows rapid problem solving, decision-making, and operational simplicity. Major existing challenges during field operations are (a) the complexity of the background chemical environment, (b) potential instrumentation drawbacks/limitations, and (c) the complexity of the nature of targeted sample compounds."

The laws of physics dictate that the concentration of a gas emitted from a point source decrease with the cube of the distance from the source and area affected by wind direction and velocity. In terms of identifying a source of illicit material, this means that sampling has to take place as close as possible to the point source. The analysis, however, should be performed as far away as possible to reduce the risk of harm or loss of inventory and personnel.

For field and for laboratory settings, most prior art explosive detection methods for trace level detection require proximate contact between the sample and the analyzing device and/or pre-concentration of the sample, as described in Mayhew C., et al. (2010) Applications of proton transfer reaction time-of-flight mass spectrometry for the sensitive and rapid real-time detection of solid high explosives. Int. J. Mass Spec. 289, 58-63.

According to the authors of the referenced article, a heated inlet had to be employed and cold spots had to be avoided in order to detect the parent ion. Furthermore, traces of explosives were still observed to be present in the inlet system many tens of minutes after the vapor of a particular explosive had been introduced into the sample inlet lines. These are major shortcomings of current systems. Another issue are intra-lab variations due to artifacts and reliance on internal laboratory controls as described in Wolkoff (1995) Volatile Organic Compounds Sources, Measurements, Emissions, and the Impact on Indoor Air Quality. Indoor Air 5, 5-73.

As explosives behave very much like ordinary (semi) volatile organic compounds (VOCs), the same problems of sampling apply. When sampling VOCs, three main options exist:

(a) Application of media that physically or chemically bind the target compounds,
(b) Application of a storage device such as a canister,
(c) Collection through a tube.

The first two methods result in discontinuous analyses that provide either average compositions over a period of time or a snap shot in time; both require the transfer of the material to the analytical instrument. Using a tube directly connected to the analytical instrument that can perform continuous analyses allows for real-time detection of target compounds.

The size and material choice of the tubing is of essence for a successful and reliable analysis with small to no memory effects. Memory effects occur if the sampled material adheres to the wall material of the tube and gets released later into the sample stream either due to physical force or chemical reactions; this is one of the primary reasons for false positives with air monitoring. The approach to detecting explosives has not changed over the last decade, since introduced in the 1990s, "In the mobile detector air samples were sucked into the ion source through a PTFE-lined, heated tube" as described in Yinon J. and Zitrin S. (1996) Modern Methods and Applications in Analysis of Explosives. John Wiley & Sons, 316 pp. https://books.google.com/books?isbn=0471965626. It is generally believed that heavy molecules are adsorbed by the transport tubing for sampling line lengths of over a few feet. Most tests are performed with tubes on the order of a few feet at indoor conditions. To address this sampling problem, some approaches try to perform the modification of the material into an ionic stage first and then transport the ions over a distance. The maximum reported length of such an ion transportation tube is still less than ten feet. See Cotte-Rodriguez and Cooks (2006) Non-proximate detection of explosives and chemical warfare agent simulants by desorption electrospray ionization mass spectrometry. Chem. Commun. 28, 2968-2970.

Within the analytical techniques for trace VOC detection, mass spectrometry has become the method of choice. In general, an air sample is ionized and then redirected using magnetic fields into a mass distinguishing spectrometer. The method of ionization has the largest impact on the integrity of any given substance when being analyzed with this method. So-called chemical ionization techniques are designed to keep molecules from fragmenting entirely while getting charged. One of these techniques involves proton-transfer reactions (PTR) which in combination with a mass spectrometer (MS) results in the method called Proton Transfer Reaction Mass Spectrometry (PTR-MS). As described in patents DE1995149144 and WO2014/053540 A1 and references cited therein, PTR-MS uses water or other small ions to generate primary ions that then protonate the target materials within the air sample. One of the main advantages of PTR-MS over other soft-ionization techniques is the lack of need for a carrier gas. Remote and independent operations are much more effective without the need for gas cylinders or other sources of carrier gas. Because many explosives have low volatility, it is often stated that collection of these in air sampling systems require heated lines for effective transfer and high voltages to ionize them. Mayhew C., et al. (2010) Applications of proton transfer reaction time-of-flight mass spectrometry for the sensitive and rapid real-time detection of solid high explosives. Int. J. Mass Spec. 289, 58-63 states that for general explosives detection one needs to be aware of that "Given the low vapor pressures associated with the solid explosives, additional procedures were adopted to help obtain higher VOC concentrations. This involved devising and utilizing a simple pre-concentrator and thermal desorption system." In addition, "The sample inlet lines were both of approximately 1 m in length and passed from the sample to the PTR inlet system. They were heated and maintained at 120° C. to minimize surface adsorption." A different study described in Jiirschik S., et al. (2010) Proton transfer reaction mass spectrometry for the sensitive and rapid real-time detection of solid high explosives in air and water. Anal Bioanal Chem. 398, 2813-2828 used rather similar conditions: "In the case of a gas phase sample, the analyte is introduced via a gas inlet system with an adjustable flow of between 50 and 1,000 sccm and an adjustable temperature of between 40° C. and 150° C.". However, the heating of the tubes and the associated voltages in the ionization chamber cause fragmentation of the TATP molecule. TATP starts fragmenting at temperatures of >145° C. See Matyas R. and Pachman J. (2016) Primary explosives. Springer, 360 pages which makes inlet systems of that kind problematic for this target.

In view of the foregoing, it is apparent that there remains a critical need for an effective method and associated apparatus to, in prompt accurate fashion, monitor an air sample for the presence of TATP with the present invention having met this need.

It is an object of the present invention to provide a method and apparatus for continuous monitoring for TATP employing mass spectrometry.

It is another object of the present invention to provide such a system which is structured to be portable and be used as a security device at various remote locations for long periods of time or to be used at stadiums and arenas during events.

It is a further object of the invention to provide such a system which can be mounted on vehicles and drones and perform tests on samples from the vehicle or drone.

It is a further object of the present invention to provide a method and apparatus for real time or near real time monitoring for TATP.

It is another object of the invention to employ specific electronic conditions for a chemical ionization approach to such spectrometer monitoring.

It is a further object of the invention to employ specific electronic conditions for a chemical ionization approach to such spectrometer monitoring.

It is a further object of the present invention to provide a PTR-MS system providing chemical ionization where molecules are charged in an environment where primary ions are available for ionization of the molecule.

It is a further object of the invention to employ an inlet tube to deliver the sample to the ionization chamber.

It is another object of the present invention to resist excess fragmentation by controlling energy input within said ionization chambers.

It is yet another object to provide a system capable of mass spectrometer monitoring by testing two or more samples simultaneously.

It is a further object of the present invention to employ PTR-MS to maximize protonation of ions to produce enhanced results from the mass spectrometer receiving the same.

It is another object of the present invention to provide a method and related apparatus for simultaneously permitting analysis of vastly different molecules.

It is another object of the present invention to provide such a system wherein a validation cycle is provided in order to further analyze a segment of the original sample and reduce false positives in order to validate the results.

It is yet another object of the present invention to provide such a system which does not require the use of a carrier gas.

It is another object of the present invention to reduce false responses due to the lack of a memory effect in the sampling tube.

It is yet another object to provide for sensitive analysis of TATP without meaningful loss of or modification to the sample during transport from its source to introduction to the processing instrument.

It is yet another object of the present invention to provide a system which employs simultaneous chemical ionization and analysis of labile compounds which require low energy conditions and higher energies for compounds that require such energies to ionize effectively.

These and other objects of the invention will be more fully understood from the following detailed description of the invention on reference to the illustrations appended hereto.

BRIEF DESCRIPTION OF THE DRAWINGS

FIG. 3 (a) is a combination schematic and block diagram of a validation module of the invention.

FIG. 3 (b) shows schematically the valve 42 in the regular mode.

FIG. 3 (c) shows schematically the valve 42 in the validation mode.

FIG. 3 (*d*) shows schematically the valve in the storage mode.

FIG. 7 (*a*) shows the mass spectrum for m/z=223 for one moment in time.

FIG. 7 (*b*) shows the mass spectrum for m/z=91 for the same moment in time as in FIG. 7 (*a*)/

FIG. 7 (*c*) shows the rapid onset and decline in signal response to the sampling of TATP.

An analysis performed by PTR-MS depends on several parameters. The sampled air gets drawn into the ionization chamber, which is sometimes referred to as reaction chamber or drift tube. Then the air gets mixed with a stream of primary hydronium ions and based on the proton affinity of a specific compound it gets protonated or not. The parts of the air that get protonated by proton transfer reaction get pulled into the mass spectrometer where they are separated and identified by mass. The un-protonated remainder of the air gets released by the instrument. The key variables of the analysis are the volume of air drawn into the instrument over a period of time with the standard setting being 200 standard cubic centimeter per minute (sccm), the temperature of the ionization chamber, the temperature of the sample inlet which is usually set to 5° C. lower than the reaction chamber, the vacuum in the ionization chamber and the voltage applied in the ionization chamber. The temperature, the vacuum and the voltage control the reaction rate of the transfer reaction, allowing for more or less material to be protonated therefore directly impacting the detection limit of the analysis. Fragmentation of molecules creates very specific patterns of particles in the mass spectrometer for each compound. However, in a large mixture of compounds such as unfiltered air, both indoor and outdoor, fragmentation causes a huge increase in small parts that often overlap each other or are otherwise indistinguishable as to their provenance. Therefore, being able to identify the unadulterated complete molecule is a key aspect for detecting ultratrace concentrations of target molecules in air samples.

In addition, TATP is so highly fragile that it can only be protonated with minimal energy impact without causing substantial fragmentation. The fragments of TATP are, amongst others, acetone, a compound that is normally present in much larger concentrations than TATP. Applying minimal voltage to the reaction chamber will prevent too much fragmentation, but a side effect of applying low voltages in the reaction chamber is the formation of large amount of water clusters from the hydronium ions. This leaves a highly reduced amount of hydronium ions for protonating other molecules. Water clusters can also cause chemical reactions with the target molecules even further weakening the signal of a compound.

The best electronic settings of the PTR-MS when detecting explosives, the standard settings are rather well defined. As described in Sulzer P., et al. (2013), Applications of switching reagent ions in proton transfer reaction mass spectrometric instruments for the improved selectivity of explosive compounds. Int. J Mass Spec 354-355, 123-128.—"Most users of PTR-MS set the ionization chamber at a fixed reduced electric field E/N (the ratio of the electric field strength E to buffer gas number density N in the ionization chamber) of between approximately 110 Td and 140 Td (1 Td=10-17 V cm2). This range of values is considered a good compromise between minimal formation of protonated water clusters, limited fragmentation of the protonated parent species, and adequate reaction time, thereby maximizing the sensitivity for detection of a compound. When using the hydronium ion as the proton donor, its signal intensity drops dramatically for E/N values much below 90 Td (depending on humidity) owing to the formation of protonated water clusters [$H_3O^+_x$ ($H_2O$)$_n$ (n≥1)], thereby limiting the E/N values that can be used."

Using current instrumentation, one can either optimize the settings for detecting TATP or other explosives and switch between them rapidly as set forth in Sulzer P., et al. (2013) Applications of switching reagent ions in proton transfer reaction mass spectrometric instruments for the improved selectivity of explosive compounds. Int. J Mass Spec 354-355, 123-128. However, this causes the loss of information for 50% or more of the sampling time which can have tremendous implications if this causes the non-identification of an explosive-bearing source passing by the sampling inlet.

SUMMARY OF THE INVENTION

Definitions

As employed herein, the following abbreviations will have the following meanings.

TATP Triacetone triperoxide (3,3,6,6,9,9-hexamethyl-1,2,4,5,7,8-hexoxonane; CAS #17088-37-8)
TNT 2,4,6-trinitrotoluene
VOC volatile organic compounds
PTR proton-transfer reaction
MS mass spectrometer
PTR-MS proton transfer reaction mass spectrometry
PTR-Hydra PTR-MS instrument with multiple ionization chambers
EN Ratio of electric field strength to buffer gas number density in ionization chamber
PFA perfluoroalkoxy alkanes
PEEK polyether-ether-ketones
RDX 1,3,5-trinitro-1,3,5-triazine
GC-MS gas chromatography-mass spectrometry
TDU-tubes Thermal desorption unit tubes
m/z ratio of mass to charge number of ions
Sift means "Selected Ion Flow Tube" which is also a chemical ionization technique like PTR. The physics of the transfer reaction in the ionization chamber is the same.

The method and apparatus of this invention allow for the continuous and parallel monitoring of a sample for TATP through protonation by chemical ionization. Chemical ionization uses primary ions to induce a reaction of charge transfer that results in an ionized target molecule. There is minimal energetic impact in such a transfer reaction. This implies that less of the material is fragmented when reaching the mass spectrometer.

The apparatus allows for the generation of multiple streams of ions from the same air sample under different conditions of temperature, pressure and voltage within the ionization chamber. The apparatus further allows for the parallel identification of these multiple ion streams within a single mass spectrometer resulting in a single mass spectrum for the original air sample. The validation loop within the apparatus allows for instant validation of a positive identification using a subpart of the original air sample that was used for the original identification.

The invention consists of several aspects which in conjunction provide a highly versatile measurement system for TATP with the ability to reduce the chances for false positives. It consists of:

(a) the use of a sampling tube of specific material, diameter and length feasible for the detection of TATP and other explosives.

(b) Specific settings of pressure, temperature and voltage within the ionization chamber for optimal TATP detection.

(c) The design of an apparatus based on chemical ionization mass spectrometry to perform continuous monitoring of explosives in real time in parallel for substances with different proton transfer reaction conditions. For example, TATP and TNT require different settings during analysis and for validation. This approach reduces the amount of false negative results.

(d) The design of a plug-in validation module that can be introduced into any analytical air monitoring apparatus for validation of a positive identification using a subsample of the original sample material. In particular, this module can be inserted into the PTR-Hydra for direct validation of TATP or other explosives to reduce the rate of false positives.

DESCRIPTION OF THE PREFERRED EMBODIMENTS

1. "Sampling tube" or "sampling tubing" have generally been employed for the up to about 200 feet item which takes the sample from the source. "Inlet tube" or "inlet tubing" have generally been employed for the up to about 10 feet item which takes the sample from the end of the sampling tube or tubing and delivers it for processing. The term "delivery tube" will be employed to refer to the combination of a "sampling tube" and "inlet tube".

2. The words "ionization chamber" have been employed primarily in lieu of the words "reaction chamber" and "drift tube" and have been used interchangeably to refer to the portion of the system which receives the air sample from the inlet tube or inlet tubing and mixes it with the primary ion stream to produce ionized target species.

Figure 1A:
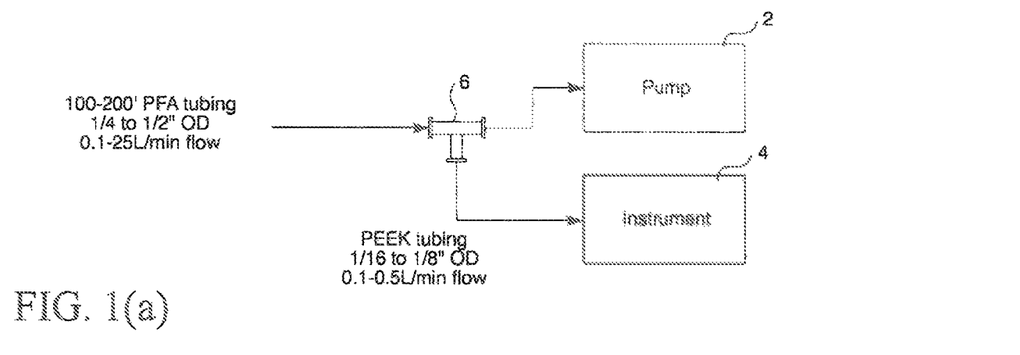
FIGS. 1(a) and 1(b) show respectively sampling configurations for different diameter external tubes which deliver the sample tested to the ionization chamber, also known as reaction chamber or drift tube.

Specific tubing provides an ideal environment for sampling TATP under field conditions. The best-suited tube material of sampling and inlet tubing for delivering of the sample to the ionization chamber was identified to be of inert plastic material, such as Perfluoroalkoxy alkanes (PFA) or Polyether-ether-ketones (PEEK). The tubes can be either made entirely of PFA or PEEK or of PFA-lined or PEEK-lined tubes made of other mantle material, such as braided steel, silicon outer cover or equivalent. For the identification of TATP, the best and most reproducible identification was found to employ a supply tube having a length of about 5 to 200 feet and, preferably, about 100 to 200 feet and, most preferably, about 5 to 100 feet of ¼" to ½" outer diameter (OD) PFA tubing and 1/16" OD PEEK inlet tubing. This method involves the use of a sampling pump to pull the air through the tube. FIG. 1(a) shows pump 2 drawing the tube delivered sample from the sampling point to the three-way connection 6. Then the vacuum system of the instrument 4 draws a sub portion through the inlet tubing to the instrument. The specifications for the sampling tubing and inlet tubing are shown to the left of the valve 6. The 1/16" PEEK tubing within the instrument is a factory setting and is subject to optimization with, e.g., ⅛" tubing.

Figure 1B:
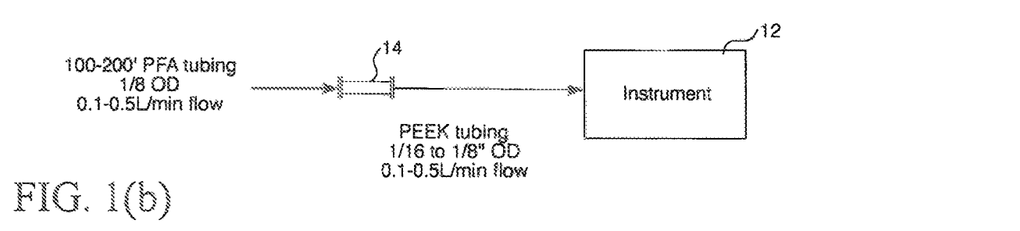

A different sampling setup would be the use of ⅛" OD PFA tubing of up to about 20 feet length with no secondary pump and the use of up to 500 sccm establishes sample of flow using the analytical instrument's internal vacuum system to draw the sample in. The ionization chamber is preferably internally heated in order to provide enhanced control of the speed and efficiency of the proton transfer reaction. In general, the warmer the heating temperature, the faster the reaction, but, however, this also increases the likelihood that fragile molecules such as PTAT will fragment. In addition, warmer temperatures make cause the molecules hitting the side of the ionization chamber being discharged and, therefore, being lost for the mass spectrometer processing. FIG. 1(b) shows said setup in a system with instrument 12 receiving the sample from the sampling tubing via connection 14 and PEEK inlet tubing. We have found that while preferred heating of the sampling tube is not required, with adequate sampling air flow, however, reductions of sampling temperature by about 36° F. or 20° C. causes a reduction in signal intensity by about 50%.

The optimal air flow through the sampling tubing for detecting TATP was found to be about 0.1 to 25 liters per minute and, preferably, about 3 to 7 liters per minute. This is the optimal condition between reducing the time of signal delay while limiting the dilution of the signal due to differences between the air flow in the sampling and the inlet tubing.

We have found that the signal response by PTR-MS for TATP can be optimized by changing to voltage and operating temperature in the ionization chamber. PTR-MS is frequently identified as PTR-TOF-MS in order to emphasize that it refers to time-of-flight mass spectrometers as contrasted with a quadruple instrument with the former effecting measurements in increments of microseconds while the latter provides increments of minutes. As for voltage, about 150-650 V are to be applied, preferably about 200-250V, the pressure shall be set to about 2.0 to 4.0 mbar, preferably about 2.1-2.3 mbar, and operating temperature of about 70-120° C., preferably about 80-100° C. An IONICON PTR-TOF-4000 and an IONICON PTR-TOF-1000ultra instruments were employed in the evaluation period and the finding would appear to be generally applicable to systems which require ionization of a vapor for identification, simply requiring optimization of their operating parameters in respect to maximum ion input to the mass spectrometer for a given amount of TATP in front of the inlet tube. The PTR-Hydra concept can be employed using components of equivalent instruments, such as the TOFWERK Vocus instruments or the SYFT Voice200 instruments.

For best results in terms of counted ions per mass material were obtained using a PFA 100 ft ⅜" tube with wall thickness of 0.065" and an air flow setting of 10 L/min. The PTR-MS inlet flow was set to 200 sccm and the inlet temperature was set to 5° C. less than the ionization chamber temperature. The optimal electronic settings in terms of ionization chamber voltage and ionization chamber temperature for TATP were found to be between 175 and 275° C. and temperatures of 80 to 120° C., preferably 215 to 235 V and temperatures of 95 to 105° C.

Under the same settings of length and diameter of external sampling tube and of the ionization chamber pressure within the PTR-MS we found the optimal voltages and temperatures to be:

(a) for TNT 600-800 V, preferably 750-800V, and a temperature of 100-140° C., preferably 120-130° C.

(b) for PETN and RDX 300-500V, preferably 375-425V, and temperatures of 80-120° C., preferably 90-110° C.

For modified PTR-MS design and PTR-Hydra-MS, the conditions and required electronic settings for identifying (a)

TATP and (b) for identifying other explosives and/or drugs are entirely different. The settings for TATP promote the formation of water clusters, therefore, preventing the protonation of other materials, which leads to huge increases in their detection limit. One way to handle the need for different settings for TATP and other explosives is described in Sulzer P., et al. (2013) by switching between settings in intervals of 5-10 seconds, but that removes the continuous monitoring aspect of the instrument. With signal durations in the range of 1-5 seconds, the chance to miss an occurrence is 50%.

Another solution is to perform continuous analyses for TATP and other compounds would be to install two or more PTR-MS instruments that are synchronized and fed from the same sampling tube. In order to reduce footprint, however, costs and synchronization issues, an integrated approach would be useful.

Figure 2:
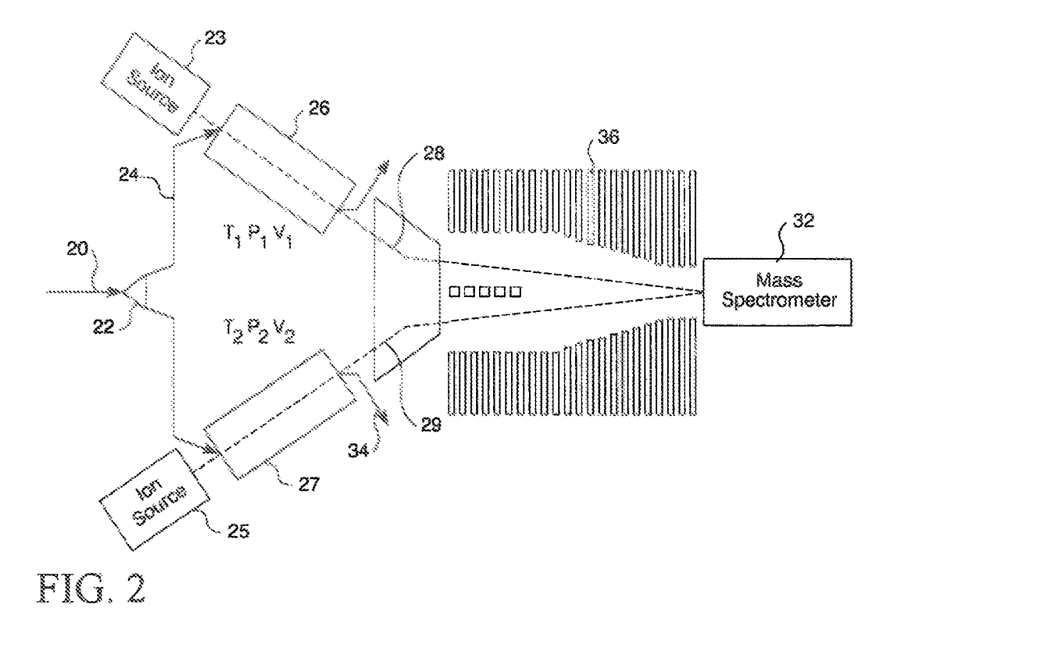
FIG. 2 is a schematic illustration of a dual inlet embodiment of the invention.

A proposed solution is a multiple inlet PTR-MS named the PTR-Hydra-MS. The design shown in FIG. 2 represents the option of a dual inlet system. The design can be expanded to at least six ionization chambers integrated, if desired. The limitations are primarily geometric due to the size of the ionization chambers and interferences of the electric fields from each ionization chamber to the next. This embodiment provides the ability to detect compounds in different ranges for the use of the multiple ionization chambers thereby permitting different compounds to be analyzed simultaneously.

The inlet tube 20 is made of material such as PEEK but materials such as PFA or equivalent may be used. The material needs to be inert to the compounds of concern to avoid fragmentation or retention of the signal. Diameters need to be in accordance to the specific instrument requirements for optimal airflow into the system. The sample is then split into equivalent portions 22 feeding into multiple inlet lines 24 of equal material, diameter and length.

The individual ion sources 23, 25 and ionization chambers 26, 27 are preferably identical to each other in terms of materials of construction, dimensions and capabilities. This aspect is important to minimize the differences of delivery of ionized species to the mass spectrometer. Although different electronic settings in the ionization chambers can cause different speeds of the ions towards the mass spectrometer, these differences are several orders shorter than the binning of the signal from the mass spectrometer. However, different lengths of the ionization chambers could cause a misalignment in the timing of ions received by the mass spectrometer that could result in incorrect identification of compounds within a specific air sample. Within the ionization chambers 26, 27 the ionization of the air molecules happens based on the specific reactions for the different types of ionization methods. For example, a proton transfer reaction or charge transfer reaction can be the driver. The resulting streams of ionized species 28, 29 are then combined into one stream by using a multiple inlet ion funnel 36 as described in U.S. Pat. No. 6,979,816 B2. The combined ion stream then gets transferred into the identification device based on mass spectrometer 32. The ion transfer may or may not include additional ion stream focusing devices such as multi-poles or ion funnels. The non-ionized air portion exits the ionization chamber at the outlet 34.

Although the individual ionization chambers 26,27 are built identically, they can be operated independently with different electronic setting and with different reaction ions. As disclosed in patent publication WO2014/053540 A1, applying different primary ions to the ionization chamber can be beneficial for ionization of target compounds.

The main parameters that can be set up individually are: internal pressure, temperature and voltage applied. One can be run with optimized conditions specific to a compound or class of compounds (T1, P1, V1 in FIG. 2) while the other is performing at conditions optimized for other compounds (T2, P2, V2). This ensures that any given package of air from the sampling line gets ionized in multiple ways with optimized conditions for the different targets.

For example, one of the chambers can be set to the optimal conditions of identifying TATP, while the others are set for optimal identification of other explosives. The settings for TATP are unique within PTR-MS applications insofar that the existence of water clusters is taken into account, making the setting rather unfavorable for any other analyte. On the other hand, the settings for identifying other explosives such as TNT cause a loss in signal response from TATP by ~40% (ideal conditions for VTATP=225V, TTATP=100° C.; VTNT=775V, TTNT=125° C.).

The preferred embodiment of this setup is with two or more ionization chambers in a setup equivalent to a PTR-MS. The ionization chambers 26, 27 may be built as an assemblage of metal rings or a glass tube with RF induction. The upper limit of the number of ionization chambers is defined by geometrical issues, electrical field interferences and the capacity of the mass spectrometer.

An alternative embodiment would be the setup with two or more ionization chambers built like a selected ion flow tube (SIFT) or equivalent chemical ionization chambers. While PTR aims at producing a single ion stream of hydroniums or other specific small ions such as O+ or NO+, SIFT aims at generating a mix of ions from ionizing ambient air with all its compounds, and then filtering this plethora of ions to a single ion stream that is then used in the ionization chamber to generate the secondary ions like a PTR. Benefit of the SIFT approach is to be able to switch between reagent ions swiftly, disadvantage is that the filtering of the ions highly reduces the overall ion flow and results in worse sensitivities. For this invention, we should include this technique and call it out specifically, since the main competitor to the PTR instruments on the commercial market is built as a SIFT instrument. And the validation loop can be included into a SIFT instrument as easily as into a PTR instrument.

Figure 3A:
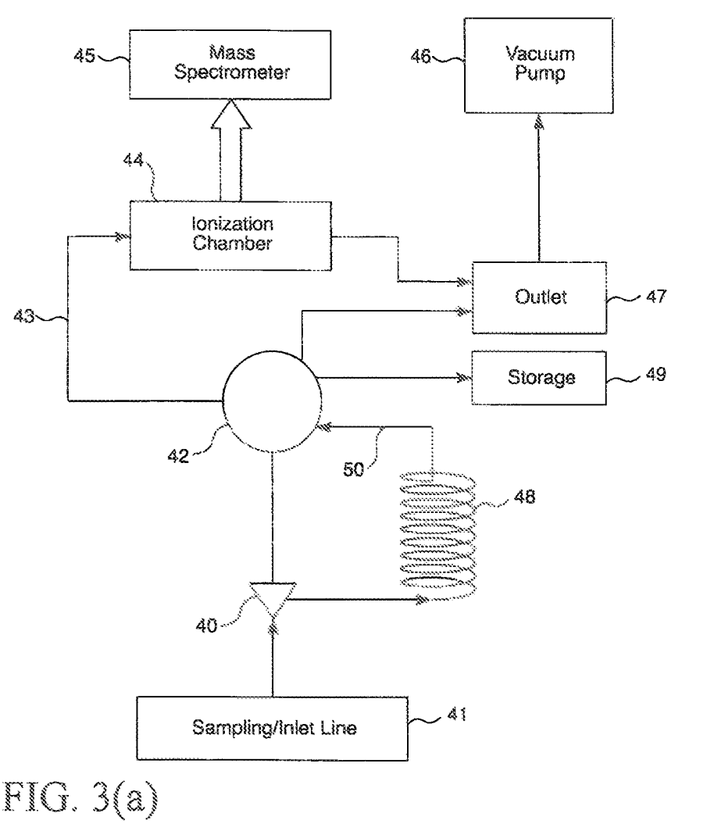

To reduce the amount of false positive identifications, i.e., a positive identifications, i.e., a positive result despite the lack of adequate material in the sample, a validation module was developed. This module is added to the common inlet system within the instrument as shown in FIG. 2 and replaces the direct inlet line 24. Referring to FIGS. 3(a) through 3 (d), the module operates in three different settings: "Standard" for normal analytical operations, FIG. 3(b); "validation" to reinvestigate an air sample with either the same or different settings of the ionization chamber, FIG. 3(c); "storage" to save the air sample for analysis at a later stage using different instrumentation (FIG. 3(d). Storage may, for example, be in a storage unit selected from the group consisting of air canisters, bags and desorption tubes. The airflow is driven by the vacuum applied to it from the instrument's internal vacuum pump 46. A portion of that airflow 46 is then introduced into the ionization chamber 44. The other portion is kept in a validation loop 48 to allow the first portion being analyzed and the second portion still available within the instrument. Upon positive identification of, e.g., TATP, the second portion can be rerouted into the ionization chamber 44 for validation. The details of this invention are displayed in FIGS. 3 (a) through 3(d) and described in detail hereinafter. The plug-in setup consists of the regular parts of a chemical ionization mass spectrometer, being an ion source, an ionization chamber, guides for the ions and a mass spectrometer to identify the mass of the ions. The inlet system normally contains an inlet that has a specific airflow, based on the vacuum applied to it. A portion of that airflow is then introduced into the ionization chamber. This inlet is the starting point of the invention shown in FIGS. 3 (a) through 3 (d).

As shown in FIG. 3(a), the inlet line 41 is split into two lines of equivalent material but different lengths, both are connected to the same vacuum pump. Valve 42 on the lines allows for transfer of air samples from the secondary line to the primary line. The primary line 43 is the one permanently connected to the ionization chamber 44. The secondary line 50 is the one that requires switching of the valve 42 to connect to the ionization chamber 44. In the description hereinafter below, the secondary line is referred to as "sample loop". For a detailed description of operation of the validation module, see FIGS. 3(a) and 4.

Figure 3B:
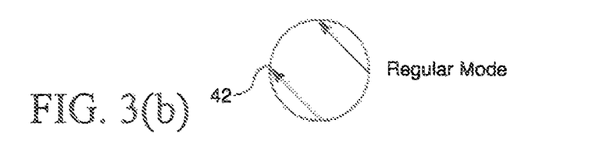
Figure 4:
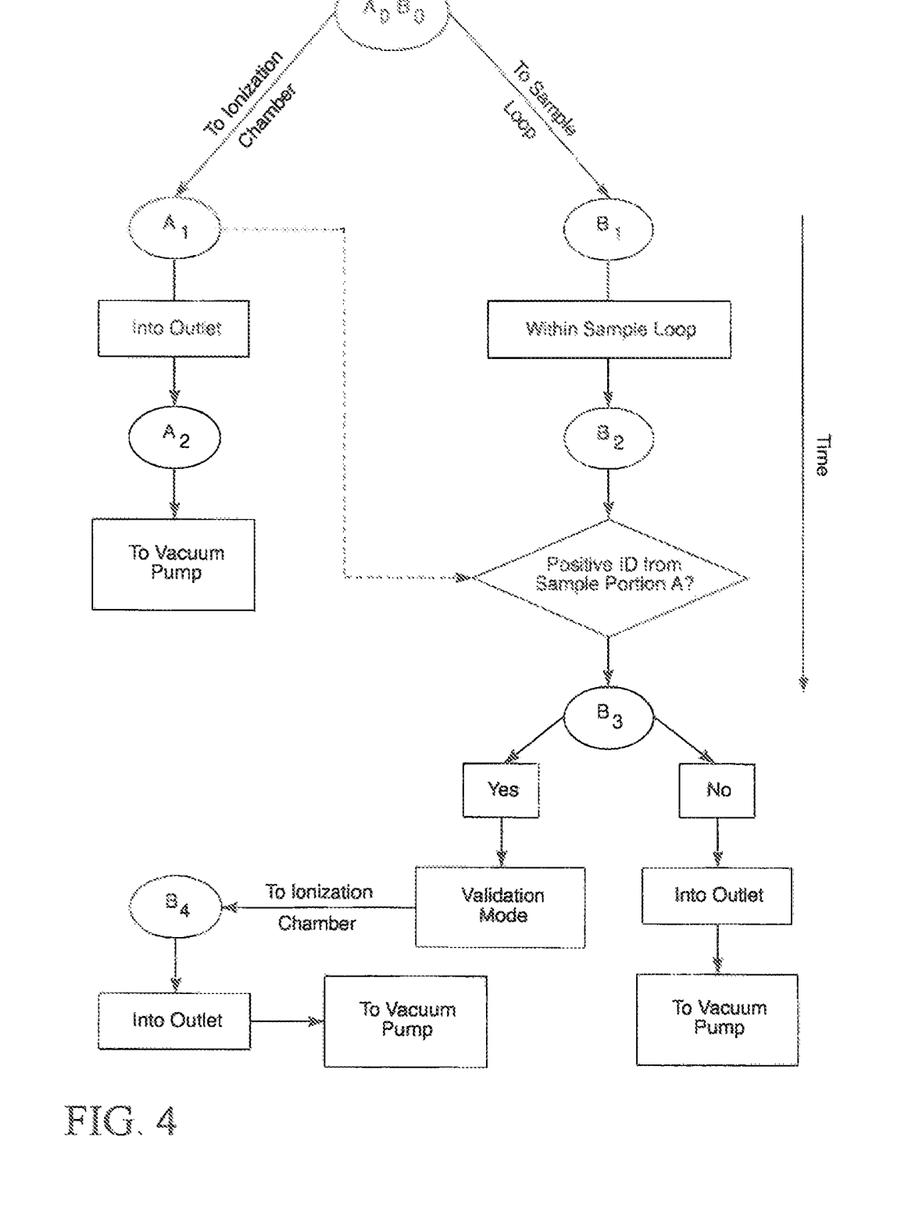
FIG. 4 is a block diagram of a validation module having two split air pockets.

Referring to FIGS. 3(a), 3(b) and 4, a sample from the sampling inlet line 41 reaches a value which is a splitting point 40, then one sample portion (A) gets transferred through the primary line via a multi-line valve 42 into the inlet line 43 into the reaction chamber 44. The ionized species from this sample gets transferred into the mass spectrometer 45 and analyzed. The non-ionized portion of (A) gets transferred via the outlet 47 into the vacuum pump 46. In the meantime, sample portion (B) travels through the secondary line 48. Portion (B) gets pulled by the same vacuum from the vacuum pump 46 into the sample loop 48. The loop 48 is preferably made of the same inert material as the sample inlet 41, the primary line 43 and the transfer line 50, and has a length that results in a residence time of sample portion (B) within the sample loop 48 to be at least about 2-5 seconds, depending on the type of mass spectrometer 45 and its response time. Under normal operation portion (B) will then be pulled to the same vacuum pump 46 as portion (A). For optimal results, the material for the sample loop 48 needs to have no or minimal fragmentation and chromatographic effects on the target material.

Figure 3C:
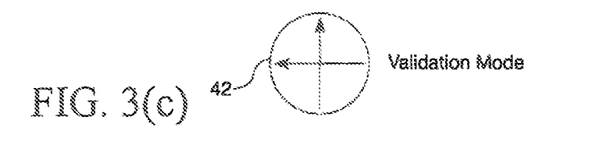

In case of a positive ID from sample portion (A) measured by the mass spectrometer 45, as shown in FIG. 3(c), the valve 42 switches to "Validation mode" and connects portion (B) to valve 42. Portion (B) then gets transferred through the inlet 43 to the ionization chamber 44, ionized and then analyzed in the mass spectrometer 45 for confirmation of the positive ID. Alternatively, valve 42 may be turned to the storage position shown in FIG. 3(d).

Referring to FIGS. 3 (a) and 4, and the validation module which serves to validate the results, indices refer to specific times, for example, $A_1$ and $B_1$ are the two split air pockets at time t=1. $A_0B_0$ is the original sample of air drawn into the sampling line.

The main benefit of this arrangement is that the same original air package is available for re-analysis in case of a positive ID of a bolus emission. This allows the change of electronic settings in the reaction chamber and/or the mass spectrometer to use optimized conditions for the potentially positively identified substance. In case the optimal conditions are already applied, it serves as a true validation to reduce false positive IDs.

For example, the positive ID of TATP using optimized conditions will result in certain peak heights of m/z 223 and 91, respectively. When validating TATP, one could increase the voltage, which will cause the amount of 223 to reduce and the amount of 91 to increase in predetermined amounts, based on the fragmentation pattern of TATP. For the positive validation of a TNT signal, the ionization chamber voltage would be increased and lead to an increased signal at m/z 228 as described in reference 21. Sulzer P., et al. (2012) Proton Transfer Reaction Mass Spectrometry and the Unambiguous Real-Time Detection of 2,4,6 Trinitrotoluene. Anal. Chem. 84, 4161-4166.

The preferred embodiments of this module are within an instrument based on Proton Transfer Reaction Mass Spectrometry (PTR-TOF-MS), Selected Ion Flow tube mass spectrometry (SIFT-MS) or more general any chemical ionization mass spectrometer. These continuous air monitoring instruments benefit the most from the ability to validate bolus emissions within seconds.

An alternative embodiment of this part of the invention would incorporate any near-real time air-monitoring devices including Gas chromatography mass spectrometers (GC-MS), cavity ring down spectrometry, or equivalent.

Figure 3D:
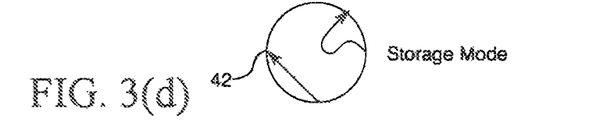

An alternative embodiment of this part of the invention could be the replacement of the connection between the primary and secondary sample line by a transfer line to air storage devices, such as Summa canisters or thermal desorption unit tubes (TDU-tubes). This kind of setup would allow the storage of a positively identified material in a long term manner for validation by a secondary technique. In some cases, the continuous monitoring analyses are not considered legally defensible, therefore requiring confirmation by accredited methods such as GC-MS. The storage of a sample of air that has a positive identification based on the continuous monitoring technique would significantly increase the efficiency of monitoring. See FIG. 3 (d). Examples would be in the environmental area such as brownfield remediation sites, law enforcement area such as monitoring of vehicles or people for drugs or explosives, or research areas for the capture of bolus emissions in combustion engine research.

Figure 5:
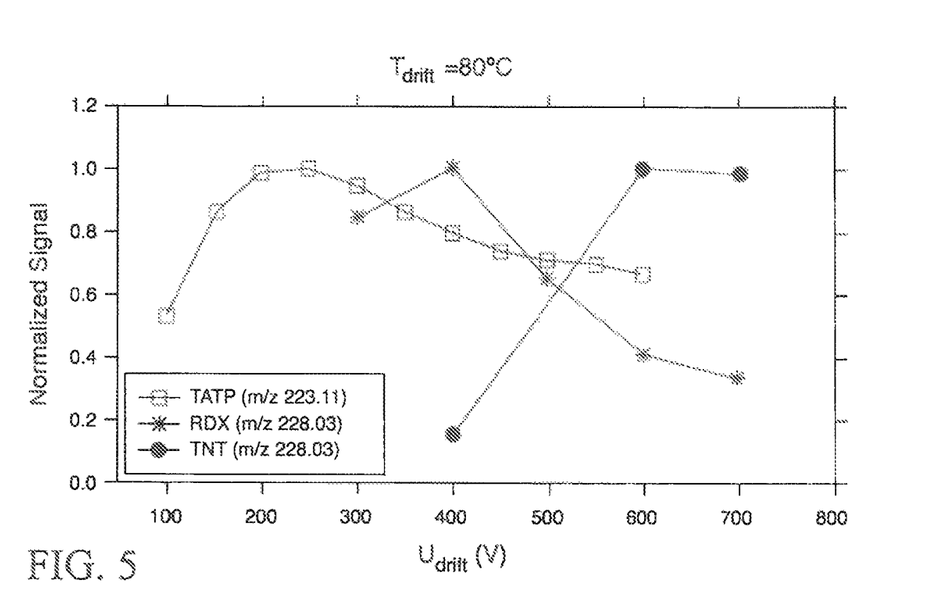
FIG. 5 shows a plot showing the optimal voltage for ionizing TATP as compared with RDX and TNT.

FIG. 5 shows a direct comparison of the impact of a specific set of conditions within the ionization chamber to the amount of ionized molecules. The "normalized signal" shows counts per second as measured in the mass spectrometer normalized to the maximum amount of counts for each compound. The temperature and pressure are fixed in this graph to 80° C. and 2.2 mbar, respectively, with variable voltages V. The best voltage setting for TATP at 200-250V would not produce any TNT or RDX at ionized molecules and, therefore, these compounds would not be detectable. At the best voltage for RDX at 400V, TNT would only produce approximately 15% of its max intensity, therefore, likely causing false negative results. In addition, TNT tends to ionize significantly better at temperatures that are above the thermal disintegration of 145° C.

For reproducible identification of TATP using hydronium as the ionizing agent, the two masses m/z=223 and 91 are the best choice. There are no other compounds likely to be in an ambient environment with parent masses near 223 and a fragmentation pattern containing 91. One of the few compounds that are quite prevalent in the environment with m/z=223 is Diethylphthalate; another is Hexamethylcyclotrisiloxane. The first is a semi-volatile with a low vapor pressure, but it may show up if found at a location of high concentration; however, it shows essentially no fragmentation, specifically not at m/z=91. The second substance can be found in household items but also does not fragment into m/z 91. In case the preparation of the TATP used ammonium containing substances or ammonium is used as the ionizing agent instead of hydronium, mass m/z=240 is the mass of the un-fragmented molecule. This can be taken into account when working with material of unknown provenance.

The other fragments with prominent peaks, such as (in decreasing intensity) m/z=59, 61, 43, 89, 74, 75 are either nondistinguishable from common VOCs in air such as acetone, or are close/overlapped by water clusters.

EXAMPLES

Figure 6:
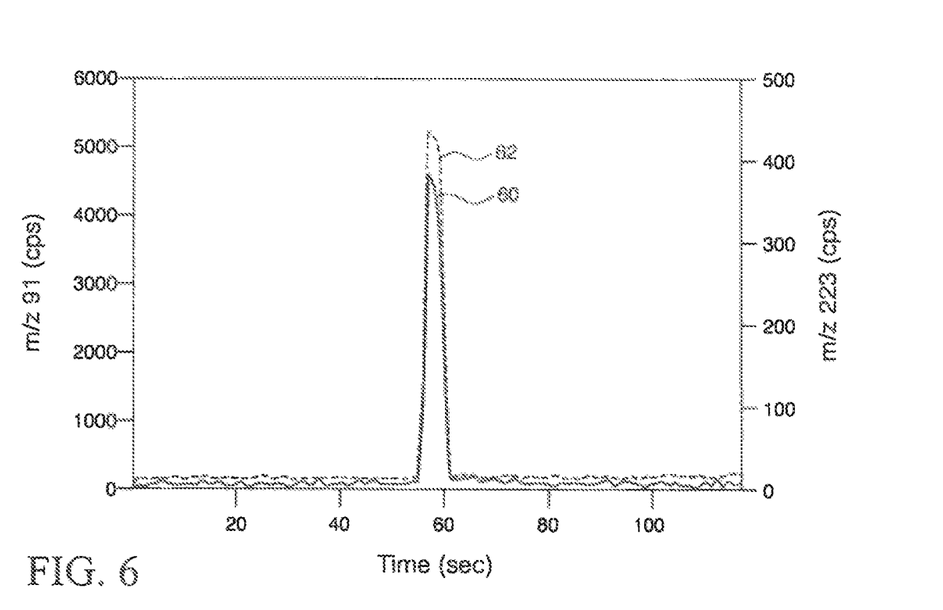
FIG. 6 shows a plot of the response of 0.5 g of TATP in an air volume equivalent to an automobile at m/z 223 (complete molecule) and m/z 91 (fragment).

This example involves a demonstration setup with a 0.5 g open canister of TATP on an air volume equivalent to the volume of a compact car. The ambient temperature was in the low 40° F.s, and the air volume was heated for 5 minutes of air at 72° F. with the open canister in place. The scenario was designed to imitate a checkpoint situation where the driver would open the side window and the end of a 100 feet ⅜" sampling tube disguised within the sleeve of the jacket of a guard person would be guided towards the airspace. The end of the tube was approximately 6" from the opening representing an open car window. The graph shown in FIG. 6 shows the response of both parent mass 223 and primary fragment mass reading 91 shown respectively as reference numbers 60 and 62. The measurements were performed using the optimized electronic conditions for TAPT analyses described hereinbefore.

The next example involves detection of TATP at 6" distance from the end of a tube.

This case shows the speed in response and the specificity of the signal at mass 223.

Figure 7A:
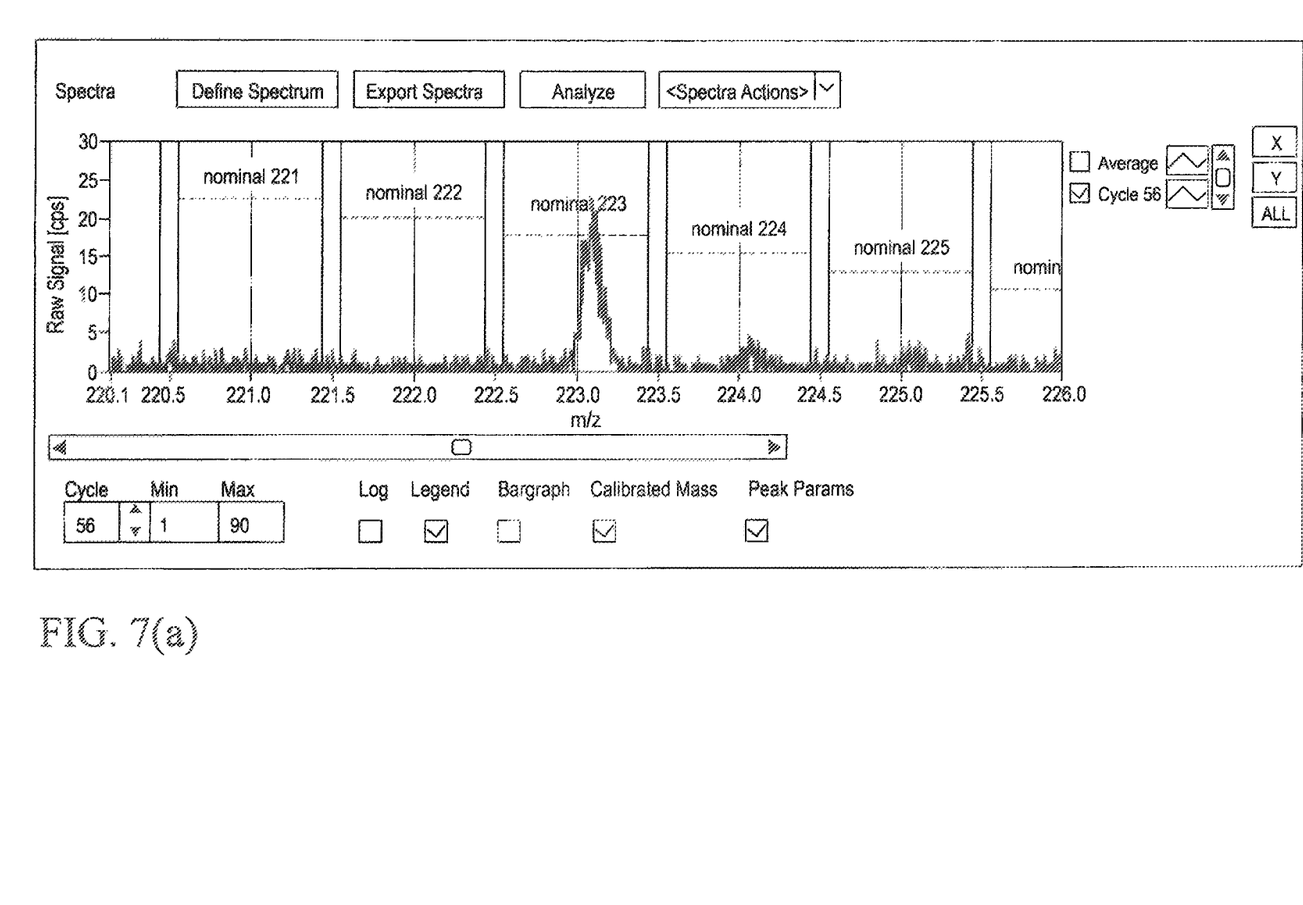
Figure 7B:
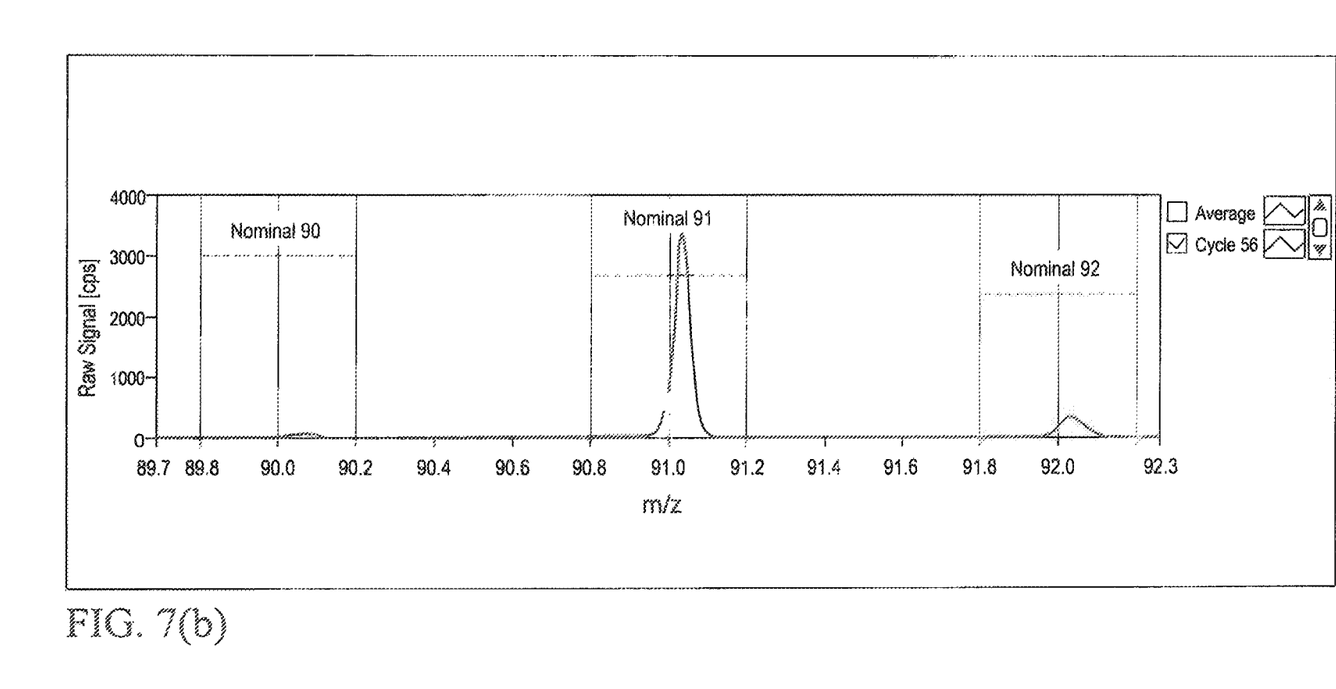

FIG. 7(a) shows the mass spectrum for one specific moment in time. This shows the narrow peak of m/z=223. FIG. 7(b) shows the graph of the same moment in time at mass m/z=91. The peak is significantly larger than for m/z-223 The system will provide a positive reading for the presence of TAPT when an analysis results in both a readout of 223 for the primary molecule and a readout of 91 for the primary fragment. Both ions must be present in order to conclude that TAPT is in the sample. In case of lack of mass m/z 223, and a high presence of m/z 91, it is beneficial to evaluate the presence of mass m/z 240, which represents the complete molecule with an ammonium substitution. The quantity of TATP present correlates with the amount of counts per second at a given m/z value. This relates directly to the size of the peaks such as those shown in FIG. 6. The counts per second create a spectrum of peaks such as that shown in FIGS. 7 (a) and (b).

The primary readout from the mass spectrometer are the counts per second per mass. This is a converted result from the actual parameter measured which is the duration between a pulse set at the beginning of the mass spectrometer and the arrival of the ion at the detector at the end of the spectrometer read. The narrower the peak, the more precise the spectrometer works with the area underneath the peak being employed for quantitative analysis.

Figure 7C:
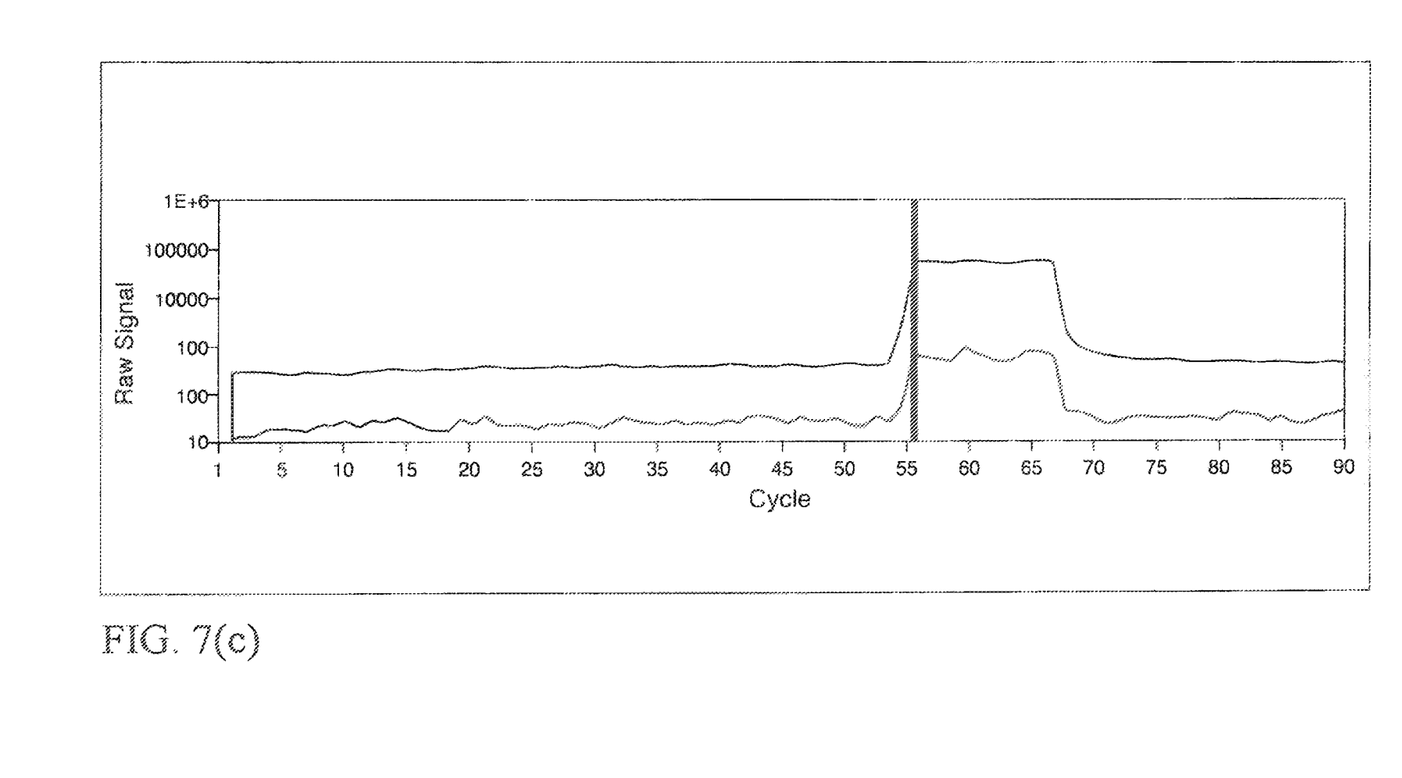

In FIG. 7(c), the two masses m/z=223 and 91 are displayed over time. It shows that the onset of the signal is within 1-2 seconds with basically no memory effect; the signal drops to background within the same time frame as the onset. A lack of memory effect using the PFA tube is essential for security applications to reduce false positive responses.

Figure 8:
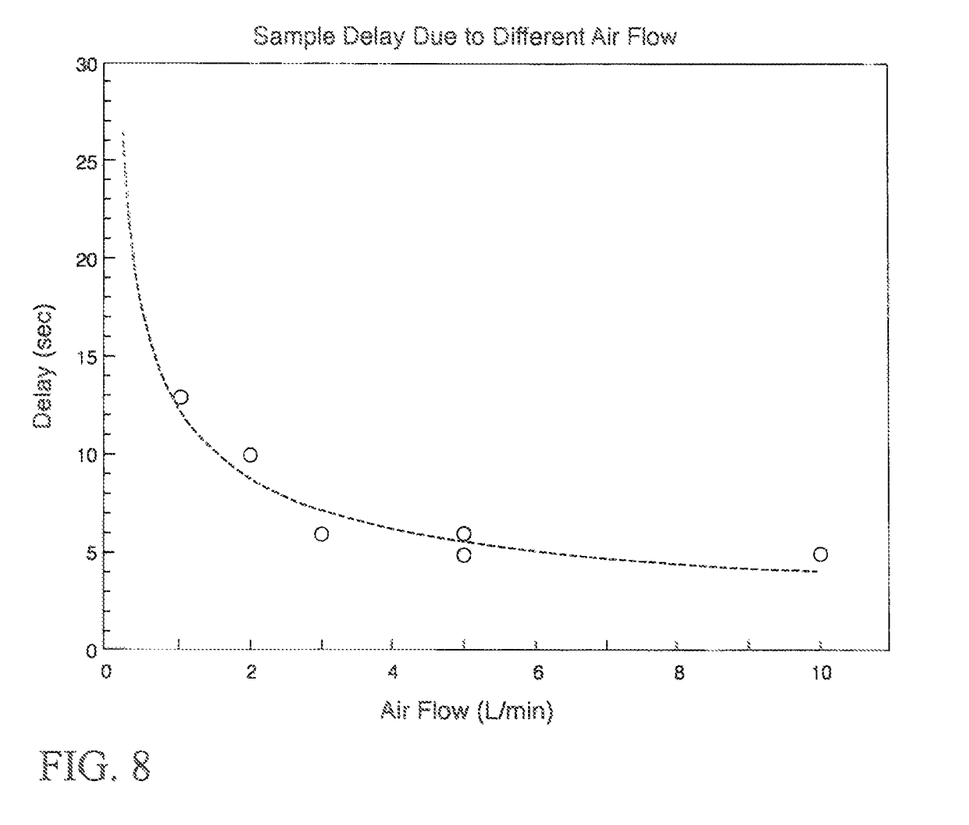
FIG. 8 is a plot showing sample delay due to varying air flow when using a 100 feet tube of ⅜ inch outer diameter made of PFA.

The graph of FIG. 8 shows the relationship of air flow within sampling tube and signal delay when using a 100 ft length ⅜" OD sampling tube to introduce an air sample for a PTR-MS monitoring for TATP. The sample delay due to reduced air flow can be substantial for inlet speeds of <1 L/min. This means that a reduction in sampling speed by using the internal vacuum system of the PTR-MS can increase the delay in signal response to a potential threat to up to ½ minute.

Whereas particular embodiments of the invention have been described hereinbefore for purposes of illustration, it will be evident to those skilled in the art that numerous variations of the details may be made without departing from the invention as defined in the appended claims.

What is claimed is:

1. A method of monitoring a sample for TATP while simultaneously monitoring for other materials comprising
providing a delivery tube for delivering air as said sample to an instrument,
providing said instrument with a plurality of ionization chambers, each receiving an equal portion of said sample,
said ionization chambers being structured to receive said sample from said delivery tube,
delivering equal portions of said sample under different ionization conditions to each said ionization chamber,
subjecting said sample portions to a proton-transfer reaction to generate ions which protonate target materials within said sample,
combining said portions into a single stream,
delivering said single stream of protonated ions to a mass spectrometer for determination of the m/z value,
discharging the ion protonated residual sample from said ionization chambers to the atmosphere,
if the mass spectrometer provides a reading of one of 223 and 240 for parent ions and 91 for fragments determining that TATP is present in the sample,
performing said method continuously during said monitoring, and
employing a verification cycle.

2. The method of claim 1 including
said delivery tube having a sampling tube having a length of about 5 to 200 feet, and
said sampling tube having an outer diameter of about ¼ to ½ inch.

3. The method of claim 2 including
a flow rate of said sample through said sampling tube being about 0.1 to 25 liters per minute.

4. The method of claim 3 including
the rate of flow of said sample through delivery tube being about 7 to 10 liters per minute.

5. The method of claim 2 including
the flow rate of said sample through said delivery tube being about 0.1 to 0.5 liters per minute.

6. The method of claim 2 including
not heating said delivery tube.

7. The method of claim 2 including
said delivery tube having an inlet tube having an outer diameter of about 1/16 to ⅛ inch.

8. The method of claim 2 including
said delivery tube being internally coated.

9. The method of claim 2 including
said delivery tube being composed of inert material.

10. The method of claim 2 including
said delivery tube having a sampling tube having a length of about 100 to 200 feet.

11. The method of claim 1 including
employing two said ionization chambers.

12. The method of claim 1 including
employing a multiple inlet ion funnel to combine said ions for TATP and said other materials before they enter said mass spectrometer.

13. The method of claim 12 including
processing said sample for different compounds in different said ionization chambers.
14. The method of claim 12 including
individually controlling the internal pressure, temperature and voltage for each of said ionization chambers.
15. The method of claim 1 including
heating said ionization chamber up to about 105° C.
16. The method of claim 15 including
heating said ionization chamber to about 80° C. to 120° C.
17. The method of claim 16 including
said heating of said ionization chambers being to about 95° C. to 105° C.
18. The method of claim 1 including
performing said monitoring on a real time basis.
19. The method of claim 18 including
performing said monitoring in increments between about 0.8 and 1.2 seconds.
20. The method of claim 1 including employing chemical ionization to reduce fragmentation of the molecules during ionizing.
21. The method of claim 1 including
processing fragments of said sample formed during said protonation of said sample by said mass spectrometer, and
employing the output of said mass spectrometer from said fragments in identifying the sample.
22. The method of claim 21 including
if said mass spectrometer provides a reading of 223 for the parent ions and 91 for the parent fragments determining that TATP is present in the sample.
23. The method of claim 21 including
if the said mass spectrometer provides a reading of 240 for the parent ions and 91 for the parent fragments determining that TATP is present in the sample.
24. The method of claim 1 including
employing in-situ a validation cycle by processing a second portion of said sample in one of said ionization chambers under the same ionization conditions.
25. The method of claim 24 including
employing said validation cycle when said mass spectrometer provides a positive output indicating the presence of TATP.
26. The method of claim 24 including
separating said second portion from said delivery tube before introduction into said ionization chamber.
27. The method of claim 24 including
storing said second portion of said sample.
28. The method of claim 27 including
effecting said storage of said second portion in a storage unit selected from the group consisting of air canisters, bags and desorption tubes.
29. The method of claim 1 including
said sampling tube is composed of an inert material.
30. The method of claim 29 including
said delivery tube is made of a material selected from the group consisting of perfluoroalkoxy and polyether-ether-ketones.
31. The method of claim 1 including
employing a vacuum pump to bring said sample into said ionization chamber.
32. The method of claim 1 including
employing suction from said ionization chambers to bring said sample into said ionization chambers.
33. The method of claim 1 including
said delivery tube having a sampling tube having a length of about 100 to 200 feet.
34. The method of claim 1 including
said ionization chambers operating at a voltage of about 150 to 650 volts.
35. The method of claim 34 including
said ionization chamber operating at a voltage of about 215 to 235 volts.
36. The method of claim 1 including
employing pressure within said ionization chamber of about 2 to 4 mbar.
37. The method of claim 36 including
employing pressure within said ionization chamber of about 2.1 to 2.3 mbar.
38. Apparatus for monitoring a sample for TATP while monitoring for other materials comprising
a delivery tube for delivering a sample,
employing a plurality of said ionization chambers each receiving an equal portion of said sample and being operably associated with said delivery tube for receiving said sample therefrom and creating ions therefrom,
said ionization chambers being structured to subject said equal portions of said sample to chemical ionization to protonate target materials within said sample under different ionization conditions for each said ionization chamber and to combine said portions into a single stream,
a mass spectrometer for receiving said single stream protonated ions from each said ionization chamber and determining the m/z for said sample,
said mass spectrometer is structured to provide a reading of m/z values which is one of 223 and 240 and a fragment value of 91 when TATP is present in said sample, and
said apparatus being structured perform continuously during said monitoring.
39. The apparatus of claim 38 including
said apparatus being structured to process a sample which is air.
40. The apparatus of claim 38 including
said delivery tube having a sampling tube of a length of about 100 to 200 feet.
41. The apparatus of claim 38 including
a multiple inlet ion funnel for combining the ions from each said ionization chamber before they enter said mass spectrometer.
42. The apparatus of claim 41 including
said ionization chambers being structured to individually control internal pressure, temperature and voltage for each of said ionization chamber.
43. The apparatus of claim 38 including
said apparatus being structured to provide real time monitoring.
44. The apparatus of claim 43 including
performing said monitoring on a real time basis in increments of about 0.8 to 1.2 seconds.
45. The apparatus of claim 38 including
said delivery tube having a sampling tube having a length of about 5 to 200 feet.
46. The apparatus of claim 45 including
said delivery tube being composed of an inert material.
47. The apparatus of claim 46 including
said delivery tube is made of a material selected from the group consisting of perfluoroalkoxy and polyether-ether-ketones.
48. The apparatus of claim 46 including
said sampling tube having an outer diameter of about ¼ to ½ inch.

49. The apparatus of claim 48 including
said delivery tube having an outer diameter of about ⅜ to ½ inch.

50. The apparatus of claim 38 including
a validation unit for processing another portion of said sample to confirm the accuracy of the result obtained from the original portion of said sample, and
said validation unit having a storage sample loop for storing a said portion of said sample.

51. The apparatus of claim 50 including
said apparatus having a storage container for storing a portion of said sample.

52. The apparatus of claim 51 including
said storage container being selected from the group consisting of air canisters, bags and desorption tubes.

53. The apparatus of claim 38 including
said delivery tube structured to deliver said sample to said ionization chambers under the influence of a vacuum pump.

54. The apparatus of claim 38 including
said delivery tube being composed of a material selected from the group consisting of perfluoroalkoxy and polyether-ether-ketones.

55. The apparatus of claim 38 including
said apparatus structured to provide a sample flow rate of about 0.1 to 25 liters per minute.

56. The apparatus of claim 55 including
said apparatus structured to provide a sample flow rate of about 7 to 10 liters per minute.

57. The apparatus of claim 38 including
said apparatus structured to heat said ionization chambers, and
said apparatus structured to heat said ionization chamber to about 95 to 105° C.

58. The apparatus of claim 57 including
said apparatus structured to provide an applied voltage to the ionization chambers of about 150 to 650 volts.

59. The apparatus of claim 38 including
said apparatus structured to employ the ionization chambers internal vacuum system to draw the sample into the ionization chamber without requiring the use of a separate vacuum pump.

60. The apparatus of claim 38 including
said apparatus structured to apply vacuum within said ionization chambers of about 2 to 4 mbar.

* * * * *